US009066727B2

(12) United States Patent
Catanzarite et al.

(10) Patent No.: US 9,066,727 B2
(45) Date of Patent: Jun. 30, 2015

(54) PATIENT-SPECIFIC COMPUTED TOMOGRAPHY GUIDES

(75) Inventors: Joshua B. Catanzarite, Warsaw, IN (US); Ryan J. Schoenefeld, Fort Wayne, IN (US)

(73) Assignee: MATERIALISE NV (BE)

( * ) Notice: Subject to any disclaimer, the term of this patent is extended or adjusted under 35 U.S.C. 154(b) by 110 days.

(21) Appl. No.: 13/039,498

(22) Filed: Mar. 3, 2011

(65) Prior Publication Data

US 2011/0218545 A1 Sep. 8, 2011

Related U.S. Application Data

(60) Provisional application No. 61/310,543, filed on Mar. 4, 2010.

(51) Int. Cl.
*A61B 17/90* (2006.01)
*A61B 17/15* (2006.01)
(Continued)

(52) U.S. Cl.
CPC ......... *A61B 17/155* (2013.01); *A61B 2019/508* (2013.01); *A61B 2017/568* (2013.01)

(58) Field of Classification Search
CPC ................... A61B 2017/568; A61B 2019/502; A61B 2019/508; A61B 17/17; A61B 17/1739; A61B 17/1764; A61B 17/1767; A61B 17/154; A61B 17/1675; A61B 17/155; A61B 17/15; A61B 17/157; A61B 17/1677; A61F 2240/002; A61F 2240/004; A61F 2/30942; A61F 2002/30948
USPC ................ 606/86 R, 87–90, 96–98, 102, 104
See application file for complete search history.

(56) References Cited

U.S. PATENT DOCUMENTS

| 1,480,285 A | 1/1924 | Moore |
| 2,181,746 A | 11/1939 | Siebrandt |
| 2,407,845 A | 9/1946 | Nemeyer |

(Continued)

FOREIGN PATENT DOCUMENTS

| CA | 2447694 A1 | 12/2002 |
| CA | 2501041 A1 | 4/2004 |

(Continued)

OTHER PUBLICATIONS

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

(Continued)

*Primary Examiner* — Todd Manahan
*Assistant Examiner* — Marcela I Shirsat
(74) *Attorney, Agent, or Firm* — EIP US LLP

(57) ABSTRACT

An orthopedic device for joint arthroplasty includes a patient-specific alignment guide constructed and configured for a specific patient from medical scans that show a bone surface of a bone of the patient without any overlying soft tissue. The patient-specific alignment guide includes a patient-specific inner surface configured to be offset from and mimic the bone surface and form a clearance for soft tissue overlying the bone surface. The alignment guide also includes a plurality of patient-specific contact areas configured to mate and register directly on the bone surface without intervening soft tissue for direct bone registration. The plurality of patient-specific contact areas includes non-contiguous surface contact areas.

12 Claims, 9 Drawing Sheets

(51) Int. Cl.
*A61B 19/00* (2006.01)
*A61B 17/56* (2006.01)

(56) References Cited

U.S. PATENT DOCUMENTS

| | | | |
|---|---|---|---|
| 2,618,913 A | 11/1952 | Plancon et al. | |
| 2,910,978 A | 11/1959 | Urist | |
| 3,840,904 A | 10/1974 | Tronzo | |
| 4,246,895 A | 1/1981 | Rehder | |
| 4,324,006 A | 4/1982 | Charnley | |
| 4,436,684 A | 3/1984 | White | |
| 4,475,549 A | 10/1984 | Oh | |
| 4,506,393 A | 3/1985 | Murphy | |
| 4,524,766 A | 6/1985 | Petersen | |
| 4,619,658 A | 10/1986 | Pappas et al. | |
| 4,621,630 A | 11/1986 | Kenna | |
| 4,632,111 A | 12/1986 | Roche | |
| 4,633,862 A | 1/1987 | Petersen | |
| 4,663,720 A | 5/1987 | Duret et al. | |
| 4,695,283 A | 9/1987 | Aldinger | |
| 4,703,751 A | 11/1987 | Pohl | |
| 4,704,686 A | 11/1987 | Aldinger | |
| 4,721,104 A | 1/1988 | Kaufman et al. | |
| 4,778,474 A | 10/1988 | Homsy | |
| 4,800,874 A | 1/1989 | David et al. | |
| 4,821,213 A | 4/1989 | Cline et al. | |
| 4,822,365 A | 4/1989 | Walker et al. | |
| 4,841,975 A | 6/1989 | Woolson | |
| 4,846,161 A | 7/1989 | Roger | |
| 4,871,975 A | 10/1989 | Nawata et al. | |
| 4,893,619 A | 1/1990 | Dale et al. | |
| 4,896,663 A | 1/1990 | Vandewalls | |
| 4,927,422 A | 5/1990 | Engelhardt | |
| 4,936,862 A | 6/1990 | Walker et al. | |
| 4,959,066 A | 9/1990 | Dunn et al. | |
| 4,976,737 A | 12/1990 | Leake | |
| 4,979,949 A | 12/1990 | Matsen, III et al. | |
| 4,985,037 A | 1/1991 | Petersen | |
| 5,002,579 A | 3/1991 | Copf et al. | |
| 5,007,936 A | 4/1991 | Woolson | |
| 5,030,221 A | 7/1991 | Buechel et al. | |
| 5,041,117 A | 8/1991 | Engelhardt | |
| 5,053,039 A | 10/1991 | Hofmann et al. | |
| 5,086,401 A | 2/1992 | Glassman et al. | |
| 5,098,383 A | 3/1992 | Hemmy et al. | |
| 5,098,436 A | 3/1992 | Ferrante et al. | |
| 5,108,425 A | 4/1992 | Hwang | |
| 5,129,908 A | 7/1992 | Petersen | |
| 5,133,760 A | 7/1992 | Petersen et al. | |
| 5,140,777 A | 8/1992 | Ushiyama et al. | |
| 5,150,304 A | 9/1992 | Berchem et al. | |
| 5,176,684 A | 1/1993 | Ferrante et al. | |
| 5,258,032 A | 11/1993 | Bertin | |
| 5,261,915 A | 11/1993 | Durlacher et al. | |
| 5,274,565 A | 12/1993 | Reuben | |
| 5,299,288 A | 3/1994 | Glassman et al. | |
| 5,300,077 A | 4/1994 | Howell | |
| 5,320,625 A | 6/1994 | Bertin | |
| 5,342,366 A | 8/1994 | Whiteside et al. | |
| 5,344,423 A | 9/1994 | Dietz et al. | |
| 5,360,446 A | 11/1994 | Kennedy | |
| 5,368,858 A | 11/1994 | Hunziker | |
| 5,370,692 A | 12/1994 | Fink et al. | |
| 5,370,699 A | 12/1994 | Hood et al. | |
| 5,405,395 A | 4/1995 | Coates | |
| 5,408,409 A | 4/1995 | Glassman et al. | |
| 5,415,662 A | 5/1995 | Ferrante et al. | |
| 5,438,263 A | 8/1995 | Dworkin et al. | |
| 5,440,496 A | 8/1995 | Andersson et al. | |
| 5,448,489 A | 9/1995 | Reuben | |
| 5,452,407 A | 9/1995 | Crook | |
| 5,454,816 A | 10/1995 | Ashby | |
| 5,474,559 A * | 12/1995 | Bertin et al. | 606/89 |
| 5,496,324 A | 3/1996 | Barnes | |
| 5,507,833 A | 4/1996 | Bohn | |
| 5,514,519 A | 5/1996 | Neckers | |
| 5,520,695 A | 5/1996 | Luckman | |
| 5,527,317 A | 6/1996 | Ashby et al. | |
| 5,539,649 A | 7/1996 | Walsh et al. | |
| 5,554,190 A | 9/1996 | Draenert | |
| 5,560,096 A | 10/1996 | Stephens | |
| 5,571,110 A | 11/1996 | Matsen, III et al. | |
| 5,578,037 A | 11/1996 | Sanders et al. | |
| 5,595,703 A | 1/1997 | Swaelens et al. | |
| 5,607,431 A | 3/1997 | Dudasik et al. | |
| 5,620,448 A | 4/1997 | Puddu | |
| 5,634,927 A | 6/1997 | Houston et al. | |
| 5,658,294 A | 8/1997 | Sederholm | |
| 5,677,107 A | 10/1997 | Neckers | |
| 5,681,354 A | 10/1997 | Eckhoff | |
| 5,682,886 A | 11/1997 | Delp et al. | |
| 5,690,635 A | 11/1997 | Matsen, III et al. | |
| 5,702,460 A | 12/1997 | Carls et al. | |
| 5,704,941 A | 1/1998 | Jacober et al. | |
| 5,722,978 A | 3/1998 | Jenkins, Jr. | |
| 5,725,376 A | 3/1998 | Poirier | |
| 5,725,593 A | 3/1998 | Caracciolo | |
| 5,735,277 A | 4/1998 | Schuster | |
| 5,748,767 A | 5/1998 | Raab | |
| 5,749,875 A | 5/1998 | Puddu | |
| 5,749,876 A | 5/1998 | Duvillier et al. | |
| 5,762,125 A | 6/1998 | Mastrorio | |
| 5,768,134 A | 6/1998 | Swaelens et al. | |
| 5,769,092 A | 6/1998 | Williamson, Jr. | |
| 5,786,217 A | 7/1998 | Tubo et al. | |
| 5,792,143 A | 8/1998 | Samuelson et al. | |
| 5,798,924 A | 8/1998 | Eufinger et al. | |
| 5,799,055 A | 8/1998 | Peshkin et al. | |
| 5,860,981 A | 1/1999 | Bertin et al. | |
| 5,871,018 A | 2/1999 | Delp et al. | |
| 5,876,456 A | 3/1999 | Sederholm et al. | |
| 5,879,398 A | 3/1999 | Swarts et al. | |
| 5,879,402 A | 3/1999 | Lawes et al. | |
| 5,880,976 A | 3/1999 | DiGioia, III et al. | |
| 5,885,297 A | 3/1999 | Matsen, III | |
| 5,885,298 A | 3/1999 | Herrington et al. | |
| 5,895,389 A | 4/1999 | Schenk et al. | |
| 5,899,907 A | 5/1999 | Johnson | |
| 5,901,060 A | 5/1999 | Schall et al. | |
| 5,911,724 A | 6/1999 | Wehrli | |
| 5,942,370 A | 8/1999 | Neckers | |
| 5,967,777 A | 10/1999 | Klein et al. | |
| 5,976,149 A | 11/1999 | Masini | |
| 6,033,415 A | 3/2000 | Mittelstadt et al. | |
| 6,059,833 A | 5/2000 | Doets | |
| 6,120,510 A | 9/2000 | Albrektsson et al. | |
| 6,120,544 A | 9/2000 | Grundei et al. | |
| 6,126,690 A | 10/2000 | Ateshian et al. | |
| 6,136,033 A | 10/2000 | Suemer | |
| 6,156,069 A | 12/2000 | Amstutz | |
| 6,161,080 A | 12/2000 | Aouni-Ateshian et al. | |
| 6,187,010 B1 | 2/2001 | Masini | |
| 6,195,615 B1 | 2/2001 | Lysen | |
| 6,205,411 B1 | 3/2001 | DiGioia, III et al. | |
| 6,206,927 B1 | 3/2001 | Fell et al. | |
| 6,254,604 B1 | 7/2001 | Howell | |
| 6,258,097 B1 | 7/2001 | Cook et al. | |
| 6,264,698 B1 | 7/2001 | Lawes et al. | |
| 6,273,891 B1 | 8/2001 | Masini | |
| 6,290,727 B1 | 9/2001 | Otto et al. | |
| 6,293,971 B1 | 9/2001 | Nelson et al. | |
| 6,312,473 B1 | 11/2001 | Oshida | |
| 6,319,285 B1 | 11/2001 | Chamier et al. | |
| 6,325,829 B1 | 12/2001 | Schmotzer | |
| 6,343,987 B2 | 2/2002 | Hayama et al. | |
| 6,354,011 B1 | 3/2002 | Albrecht | |
| 6,379,299 B1 | 4/2002 | Borodulin et al. | |
| 6,383,228 B1 | 5/2002 | Schmotzer | |
| 6,391,251 B1 | 5/2002 | Keicher et al. | |
| 6,395,005 B1 | 5/2002 | Lovell | |
| 6,427,698 B1 | 8/2002 | Yoon | |
| 6,459,948 B1 | 10/2002 | Ateshian et al. | |
| 6,463,351 B1 | 10/2002 | Clynch | |
| 6,475,243 B1 | 11/2002 | Sheldon et al. | |

(56) References Cited

U.S. PATENT DOCUMENTS

| | | |
|---|---|---|
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,827,723 B2 | 12/2004 | Carson |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,272 B2 | 9/2008 | Richard et al. |
| 7,468,075 B2 | 12/2008 | Lang et al. |
| 7,474,223 B2 | 1/2009 | Nycz et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,896,921 B2 | 3/2011 | Smith et al. |
| 7,935,119 B2 | 5/2011 | Ammann et al. |
| 7,938,861 B2 | 5/2011 | King et al. |
| 7,962,196 B2 | 6/2011 | Tuma |
| 7,963,968 B2 | 6/2011 | Dees, Jr. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,591,516 B2 * | 11/2013 | Metzger et al. .................. 606/88 |
| 8,668,700 B2 * | 3/2014 | Catanzarite et al. ............. 606/88 |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0109784 A1 | 6/2003 | Loh et al. |
| 2003/0120276 A1 | 6/2003 | Tallarida et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |

(56) References Cited

U.S. PATENT DOCUMENTS

| | | |
|---|---|---|
| 2004/0147927 A1 | 7/2004 | Tsougarakis et al. |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2005/0008887 A1 | 1/2005 | Haymann et al. |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0171545 A1 | 8/2005 | Walsh et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0234461 A1 | 10/2005 | Burdulis et al. |
| 2005/0234468 A1 | 10/2005 | Carson |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0267353 A1 | 12/2005 | Marquart et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0235421 A1 | 10/2006 | Rosa et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288030 A1 | 12/2007 | Metzger et al. |
| 2008/0009952 A1 | 1/2008 | Hodge |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140209 A1 | 6/2008 | Iannotti et al. |
| 2008/0146969 A1 | 6/2008 | Kurtz |
| 2008/0147072 A1 | 6/2008 | Park et al. |
| 2008/0161815 A1 | 7/2008 | Schoenefeld et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |

(56) References Cited

U.S. PATENT DOCUMENTS

| | | |
|---|---|---|
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294266 A1 | 11/2008 | Steinberg |
| 2008/0300600 A1 | 12/2008 | Guelat et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0082770 A1 | 3/2009 | Worner et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0324692 A1 | 12/2010 | Uthgenannt et al. |
| 2011/0004317 A1 | 1/2011 | Hacking et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0029091 A1 | 2/2011 | Bojarski et al. |
| 2011/0029116 A1 | 2/2011 | Jordan et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106093 A1* | 5/2011 | Romano et al. ............... 606/88 |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0224674 A1 | 9/2011 | White et al. |
| 2011/0257657 A1 | 10/2011 | Turner et al. |

FOREIGN PATENT DOCUMENTS

| | | | |
|---|---|---|---|
| CA | | 2505371 A1 | 5/2004 |
| CA | | 2505419 A1 | 6/2004 |
| CA | | 2506849 A1 | 6/2004 |

(56) References Cited

FOREIGN PATENT DOCUMENTS

| | | |
|---|---|---|
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A2 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008112996 A1 | 9/2008 |
| WO | WO-2008140748 A1 | 11/2008 |
| WO | WO 2009001083 A1 * | 12/2008 |
| WO | WO-2009001083 A1 | 12/2008 |
| WO | WO-2009025783 A1 | 2/2009 |
| WO | WO-2011018458 A1 | 2/2011 |

OTHER PUBLICATIONS

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

"Amazing Precision. Beautiful Results. The next evolution of MAKOplasty® is here," brochure. (Feb. 2009) Mako Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Charl P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

(56) References Cited

OTHER PUBLICATIONS

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazan, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS—Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung and Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

(56) References Cited

OTHER PUBLICATIONS

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

* cited by examiner

PATIENT-SPECIFIC COMPUTED TOMOGRAPHY GUIDES

CROSS-REFERENCE TO RELATED APPLICATIONS

This application claims the benefit of U.S. Provisional Application No. 61/310,543, filed on Mar. 4, 2010. The disclosure of the above application is incorporated herein by reference.

INTRODUCTION

The present teachings provide various patient-specific alignment guides for knee arthroplasty. The alignment guides are based on Computed Tomography (CT) scans or other image scans that show bone surfaces without cartilage or soft tissue of the bone surface.

SUMMARY

The present teachings provide an orthopedic device for joint arthroplasty that includes a patient-specific alignment guide constructed and configured for a specific patient from medical scans that show a bone surface of a bone of the patient without any overlying soft tissue. The patient-specific alignment guide includes a patient-specific inner surface configured to be offset from and mimic the bone surface and form a clearance for soft tissue overlying the bone surface. The alignment guide also includes a plurality of patient-specific contact areas configured to mate and register directly on the bone surface without intervening soft tissue for direct bone registration. The plurality of patient-specific contact areas includes non-contiguous surface contact areas.

The patient-specific alignment guide includes a plurality of patient-specific guiding formations having corresponding bores for guiding alignment pins or other tools therethrough. The alignment guide can be a femoral guide or a tibial guide.

The present teachings also provide a method of manufacturing a patient-specific alignment guide. The method includes forming an inner surface of a patient-specific alignment guide to conform and mimic a bone surface of a patient's bone and offsetting the inner surface to avoid articular cartilage and other soft tissue. A plurality of patient-specific contact areas for direct bone registration is formed on the alignment guide.

Further areas of applicability will become apparent from the description provided herein. The description and specific examples in this summary are intended for purposes of illustration only and are not intended to limit the scope of the present disclosure and teachings.

BRIEF DESCRIPTION OF THE DRAWINGS

The present teachings will become more fully understood from the detailed description and the accompanying drawings, wherein.

Corresponding reference numerals indicate corresponding parts throughout the several views of the drawings.

DETAILED DESCRIPTION

Figure 1A:
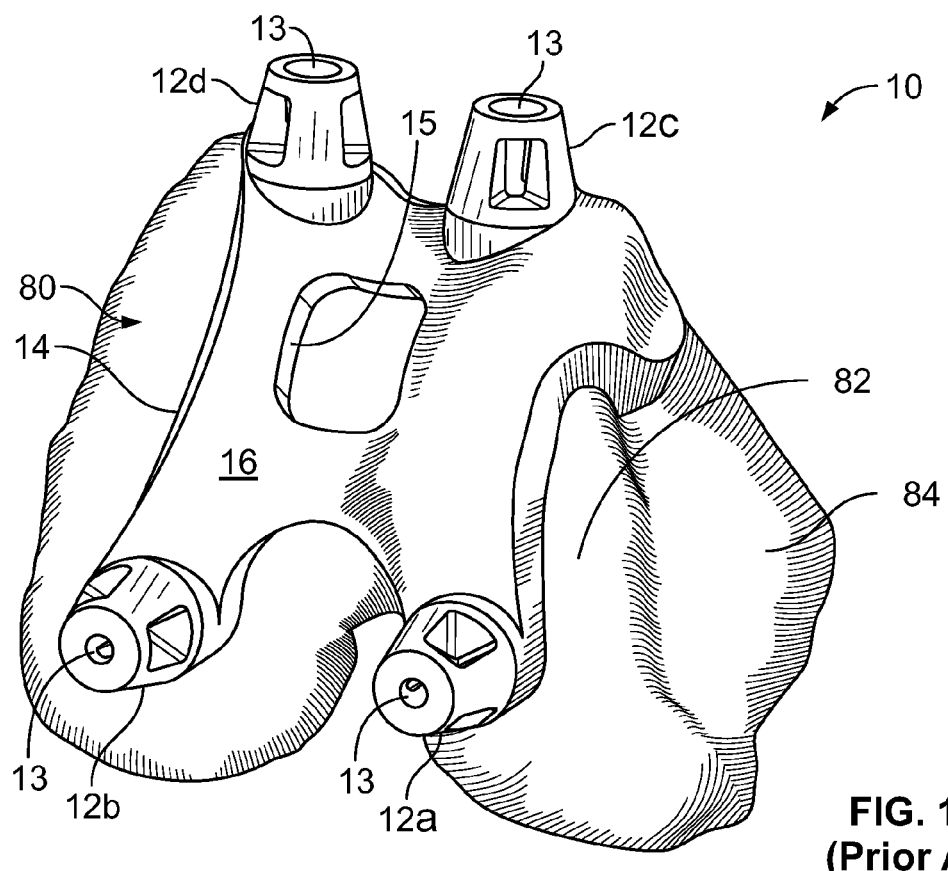
FIG. 1A is an environmental perspective view of a patient-specific femoral MRI guide.

Exemplary embodiments will now be described more fully with reference to the accompanying drawings.

The present teachings generally provide various patient-specific alignment guides for use in orthopedic surgery, such as, for example, in joint replacement or revision surgery. More specifically, the present teachings provide patient-specific femoral and tibial alignment guides that are designed based on CT (Computed Tomography) scans of the patient or other image scans that show bone surfaces without cartilage or soft tissue of the bone surface. In the discussion below and in shorthand, the patient-specific alignment guides are referenced as CT guides to indicate that they are based on image methods that show only the bone surface, even though methods other than Computed Tomography can be used.

Generally, patient-specific devices can be designed preoperatively using computer-assisted image methods based on three- or two-dimensional images of the patient's knee anatomy reconstructed from medical scans of the patient's anatomy. Various CAD programs and/or software can be utilized for three-dimensional image reconstruction, such as, for example, software commercially available by Materialise USA, Plymouth, Mich.

Patient-specific alignment guides and implants are generally configured to match a portion of the anatomy of a specific patient. The patient-specific alignment guides are generally formed using computer modeling based on the patient's 3-D anatomic image and have an engagement surface that is made to conformingly contact and match a three-dimensional image of the patient's anatomy, such as a joint surface, in only one position, by the computer methods discussed above. The patient-specific alignment guides are designed and prepared preoperatively using anatomic landmarks, such as osteophytes, for example, and can be mounted intra-operatively without any registration or other guidance based on their unique patient-specific surface guided by the patient's anatomic landmarks.

The patient-specific alignment guides can include custom-made guiding formations, such as, for example, guiding bores or cannulated guiding posts or cannulated guiding extensions or receptacles that can be used for inserting pins or other fasteners for supporting cutting tools and other instruments to perform various resections, after the alignment guides are removed and according to a surgeon-approved pre-operative plan for the specific patient.

Various alignment guides and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; U.S. patent application Ser. No. 12/025,414, filed Feb. 4, 2008, U.S. patent application Ser. No. 12/571,969, filed Oct. 1, 2009, and U.S. patent application Ser. No. 12/955,361, filed Nov. 29, 2010. The disclosures of the above applications are incorporated herein by reference.

In the instruments and surgical techniques used with the patient-specific alignment guides discussed in the commonly assigned and referenced above U.S. application Ser. No. 11/756,057, filed on May 31, 2007, holes are drilled through corresponding bores of the guiding formations and the alignment guide is removed. Alignment pins are inserted through the holes in the bone and cutting blocks can be mounted over the alignment pins to make the planned bone resections. In this manner, the holes and the corresponding alignment pins are reference elements for referencing correctly the placement of the various cutting blocks and the corresponding resections. All the alignment pins are then removed and the prosthetic components are implanted.

In the preoperative planning stage, imaging data of the relevant anatomy of a patient can be obtained at a medical facility or doctor's office, using one of the medical imaging methods described above. The imaging data can include, for example, various medical scans of a relevant joint portion or other relevant portion of the patient's anatomy, as needed for joint modeling and, optionally, for implant alignment axis determination or for other alignment purposes. The imaging data thus obtained and other associated information can be used to construct a three-dimensional computer image of the joint or other portion of the anatomy of the patient.

The patient-specific guides described herein can be manufactured by various stereolithography methods, selective laser sintering, fused deposition modeling or other rapid prototyping methods. The patient-specific guides can be made of any biocompatible material, including metal, metal alloys or plastic. Generally, the patient-specific guide is disposable and made of lightweight materials, including polymers. The patient-specific implants can be made of any biocompatible materials, including metals and alloys. The patient-specific guides, implants and associated tools can be sterilized and shipped to the surgeon or medical facility in a kit for a specific patient and surgeon during the surgical procedure.

Figure 1B:
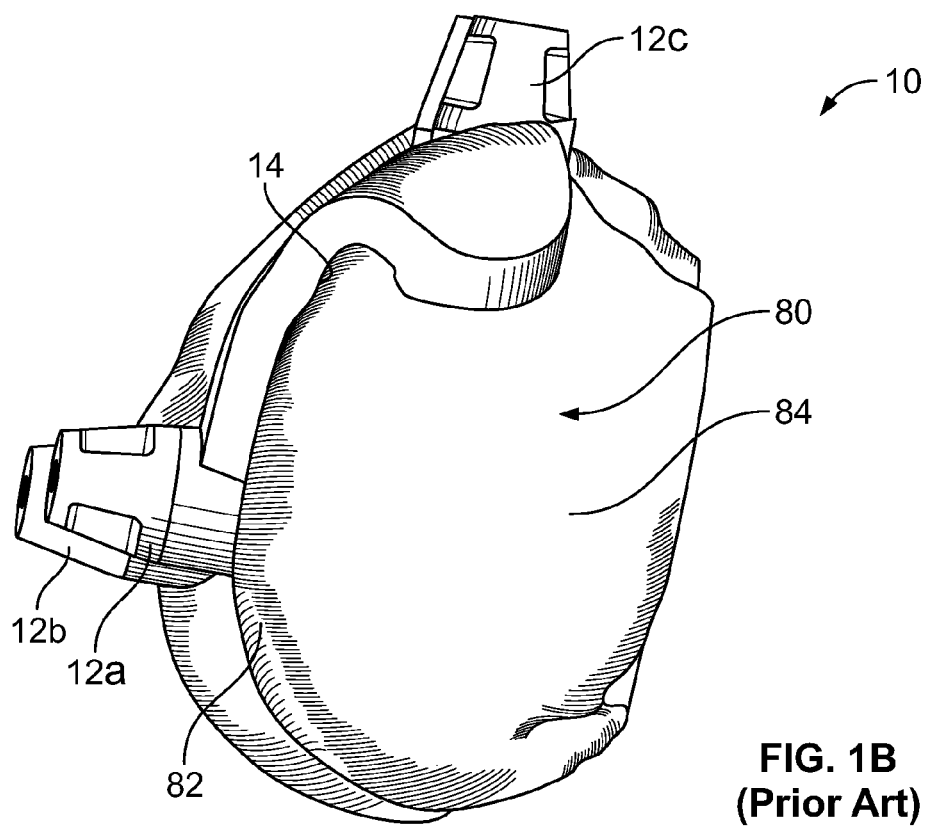
FIG. 1B is another environmental perspective view of the MRI guide of FIG. 1A.

Referring to FIGS. 1A and 1B, a prior art embodiment of a patient-specific femoral alignment guide 10 (or femoral MRI guide 10) is illustrated. The femoral alignment guide 10 is similar to femoral alignment guides described in some of the above commonly-assigned cross-referenced applications and available from assignee Biomet Manufacturing, Corp., Warsaw, Ind. The femoral alignment guide 10, as shown in FIGS. 1A and 1B, is designed based on medical scans of the patient using MRI (Magnetic Resonance Imaging). The MRI medical scans allow the joint surface to be imaged showing both the bone and overlaying soft tissue, such as articular cartilage. The femoral alignment guide 10 can be designed and configured to be mounted and nestingly conform and mated to the joint surface including the articular cartilage. In the exemplary embodiment of FIG. 1A, the femoral alignment guide or MRI guide 10 is configured to be mounted directly on the anterior surface of a femur 80 of a patient. In this regard, the femoral alignment guide 10 includes an inner surface 14 and an opposite outer surface 16. The inner surface 14 is a three-dimensional curved inner surface 14 configured to nestingly contact and engage the outer anterior surface of the femur 80 which includes both articular cartilage 82 and bone 84. The inner surface 14 is configured during the preoperative plan of the patient to fully contact, without any gaps, the outer surface of the femur 80, contacting articular cartilage 82 and bone 84 depending on what portions of the femur 80 the femoral guide 10 is configured to be mounted and contact. Because full contact is maintained, the femoral guide 10 is stably supported by the femur 80, and can be lightweight and include cut-outs or windows, such as window 15. The femoral alignment guide 10 includes four patient-specific guiding formations 12a, 12b, 12c, 12d with corresponding bores 13 for guiding alignment pins (not shown) or drilling tools, as discussed above. The guiding formations 12a, 12b, 12c, 12d (or 12, collectively) are patient-specific and designed during the preoperative plan to provide reference markers, such as alignment pins, to guide predetermined femoral resections, after the femoral alignment guide is removed. As can be seen in FIGS. 1A and 1B, the guiding formations 12a-12d can be in the form of conical elements with or without windows for providing stability for inserting alignment pins or drilling holes.

In contrast to the MRI guide 10, and referring to FIGS. 1C-13, the present teachings provide various patient-specific alignment guides 100, 200, 300, 400 (or "CT guides") that are designed based on CT scans of the patient that image only the actual bone of the patient and not any articular cartilage or other tissue overlying the bone. The CT guides 100, 200, 300, 400 are designed during the preoperative plan to have a corresponding inner surface 104, 204, 304, 404 that mimics, conforms and references the underlying bone, but with an offset, or gap that provides clearance for articular cartilage or other soft tissue without contacting such tissue where it occurs on joint surface. Rather, the CT guides 100, 200, 300, 400 are designed and configured to include structural elements that contact the patient's anatomy in discrete locations where only bone is found, providing direct bone registration, as discussed below in further detail. It is noted that in the illustrations of FIGS. 1-13, the various guides are shown on physical three-dimensional models of the corresponding bone of a specific patient. The physical models can be generated, for example, by rapid prototyping, during the preoperative plan of the patient based on the medical scans of the patient.

Exemplary embodiments of patient-specific CT guides discussed below include a patient-specific femoral anterior-medial CT guide 100 illustrated in FIGS. 1C, 1D, 2, 2A, 3 and 4; a patient-specific femoral direct anterior CT guide 200 illustrated in FIGS. 5-7A; a patient-specific tibial anterior-medial CT guide 300 illustrated in FIGS. 8-10; and a patient-specific tibial direct anterior CT guide 400 illustrated in FIGS. 11-13. Similar elements are referenced with similar numerals XYY, wherein X is 1, 2, 3 or 4 depending on the corresponding CT guide 100, 200, 300 or 400. For example, each of the CT guides 100, 200, 300, 400 can include four corresponding guiding formations 102 (or individually 102a, 102b, 102c, 102d), 202, 302 and 402 respectively. These guiding formations 102, 202, 302 and 402 can be similar to the guiding formations 12 of the MRI guide 10 of FIGS. 1A and 1B. Each guiding formation includes a corresponding bore 103, 203, 303, 403 for guiding an alignment pin or a drill bit or other tool.

With continued reference to FIGS. 1C-13, each of the CT guides 100, 200, 300, 400 can include a corresponding inner surface 104, 204, 304, 404 and an opposite outer surface 106, 206, 306, 406. As discussed above, the inner surface 104, 204, 304, 404 of each CT guide 100, 200, 300, 400 is designed during the preoperative plan and configured to mimic or mirror the underlying bone surface shown in the CT scan images, but with an offset that creates a clearance or gap to accommodate intervening articular cartilage or other soft tissue in areas where such tissue is found (or retained) over the bone. Exemplary gaps are referenced with numerals X3Y and described below for each CT guide 100, 200, 300, 400 (X=1, 2, 3, 4). Similarly, patient-specific contact areas with the bone for direct bone registration (without intervening soft tissue) are referenced with numerals X2Y and described below for each CT guide 100, 200, 300, 400 (X=1, 2, 3, 4).

Figure 1C:
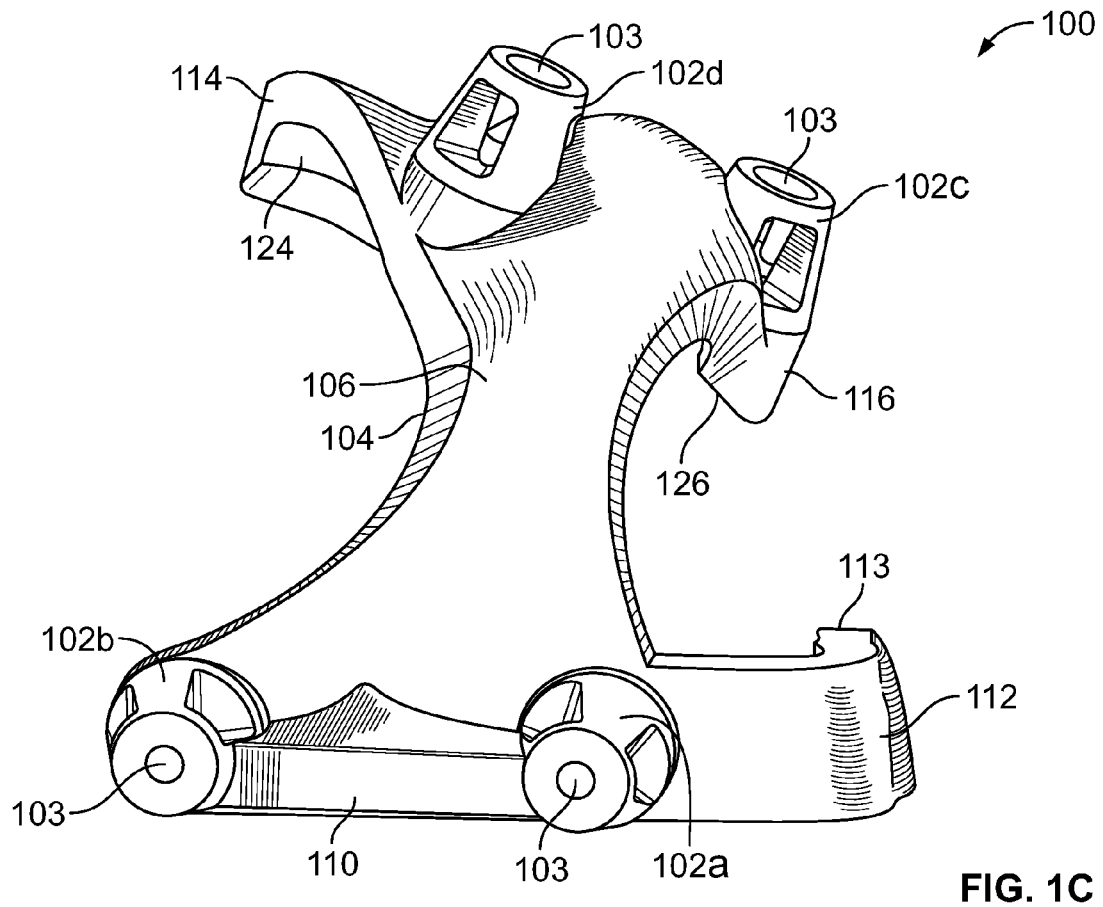
FIG. 1C is a perspective view of a patient-specific anterior-medial femoral CT guide according to the present teachings.
Figure 1D:
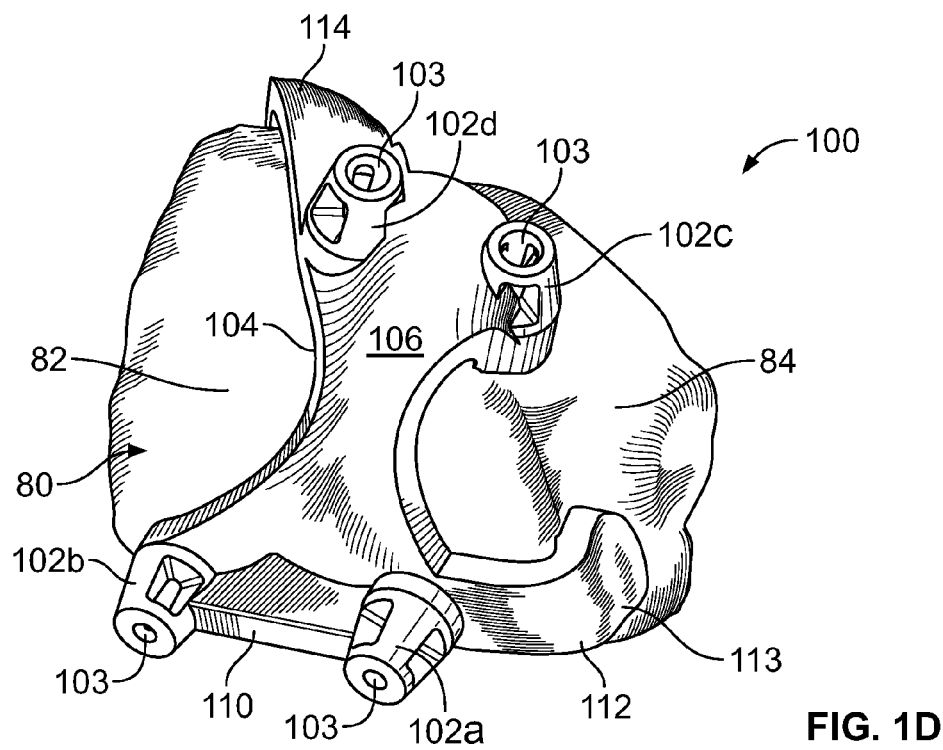
FIG. 1D is an environmental perspective view of the patient-specific anterior-medial femoral CT guide of FIG. 1C.

With continued reference to FIGS. 1C-13, each of the CT guides 100, 200, 300, 400 can also include a corresponding connection or bridge or reinforcement element 110, 210, 310, 410 between a pair of medial and lateral guiding formations for reinforcement and added stability. The bridge or reinforcing element 110, 210 extends between the pair of distal guiding formations (102a, 102b), (202a, 202b) of the corresponding femoral CT guides 100, 200. The bridge element 310, 410 extends between the pair of anterior guiding formations (302a, 302b), (402a, 402b) of the corresponding tibial CT guides 300, 400. For example, the bridge or reinforcing element 110 of femoral CT guide 100 extends between the distal formations 102a, 102b, as shown in FIG. 1C. The description of similar elements through the various embodiments will not be repeated, except when there are differences in these elements between embodiments.

Referring to FIGS. 1C, 1D, 2, 2A, and 3-5, various views of a femoral CT guide 100 for anterior-medial placement on the patient's femur 80 are illustrated. As discussed above, the reinforcing element 110 extends between the pair of distal guiding formations 102a, 102b. Additionally, an arm 112 extends medially from the femoral CT guide 100 adjacent the medial distal guiding formation 102a with a pad portion 113 forming an L-shape with the arm 112 for direct contact on the medial surface of the femoral bone 84 for direct bone registration.

Figure 2:
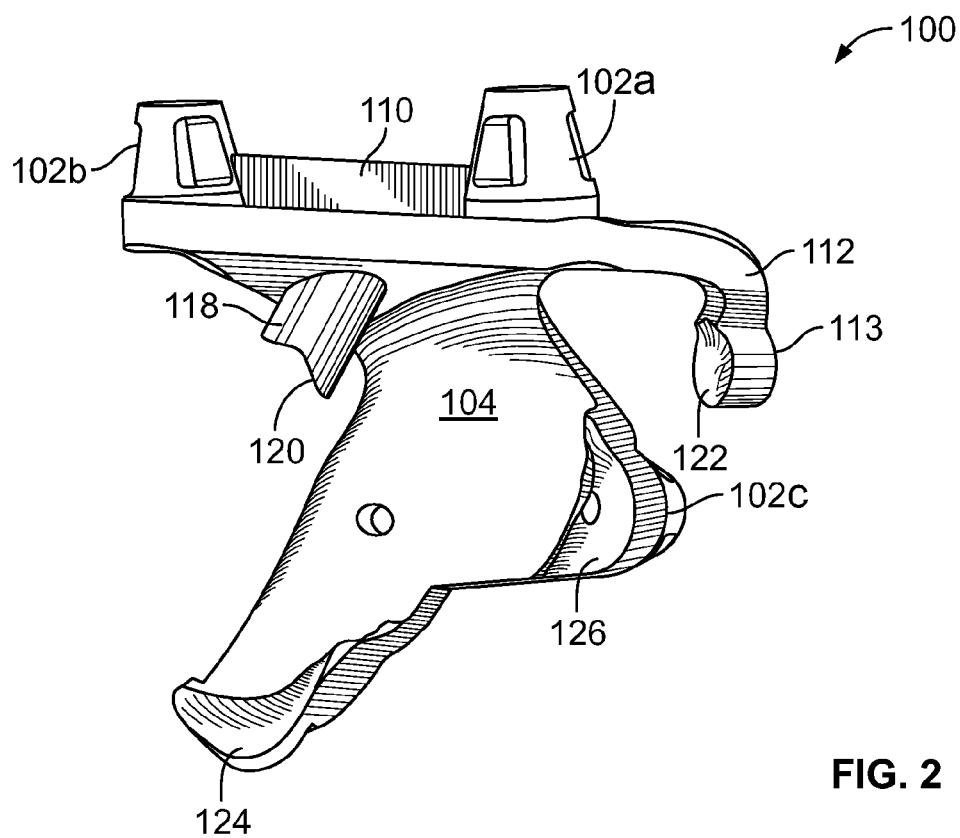
FIGS. 2 and 2A are bottom perspective views of the patient-specific anterior-medial femoral CT guide of FIG. 1C.
Figure 2A:
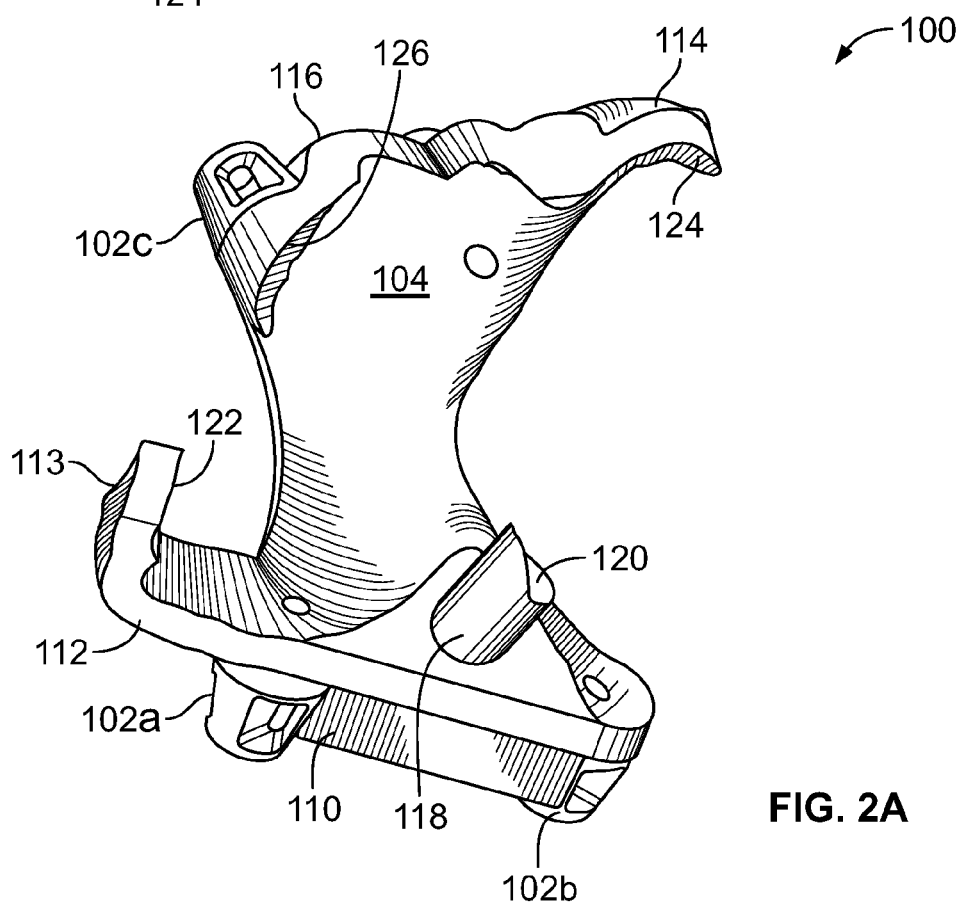
Figure 3:
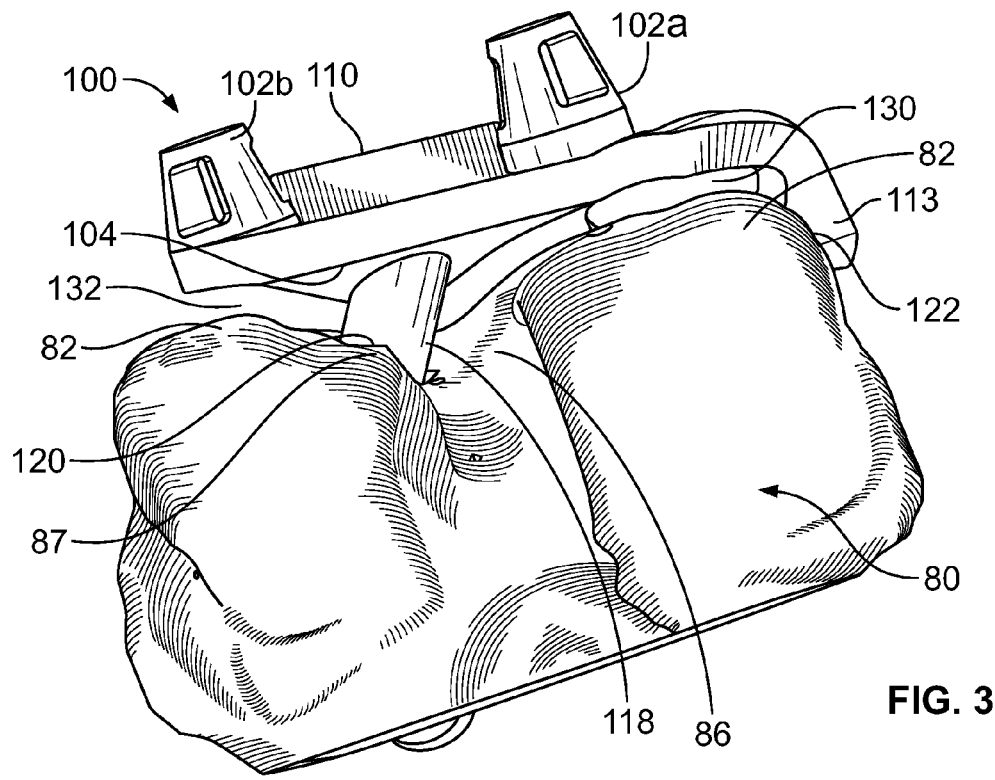
FIGS. 3 and 4 are additional environmental perspective views of the patient-specific anterior-medial femoral CT guide of FIG. 1C.
Figure 4:
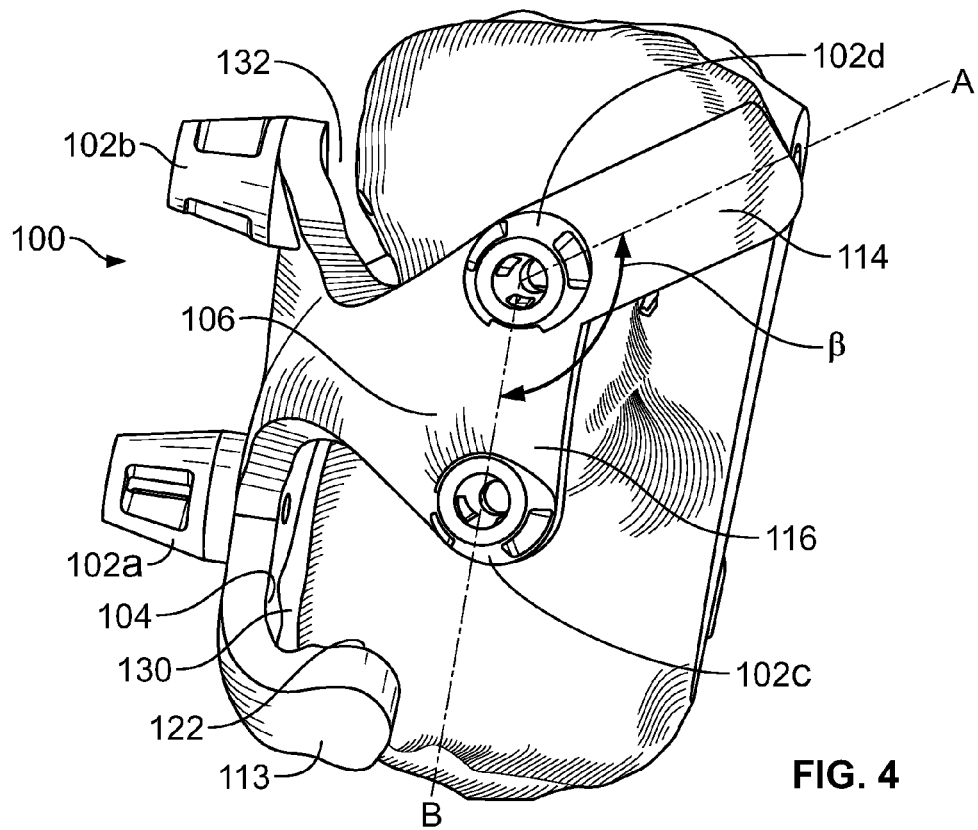
Figure 5:
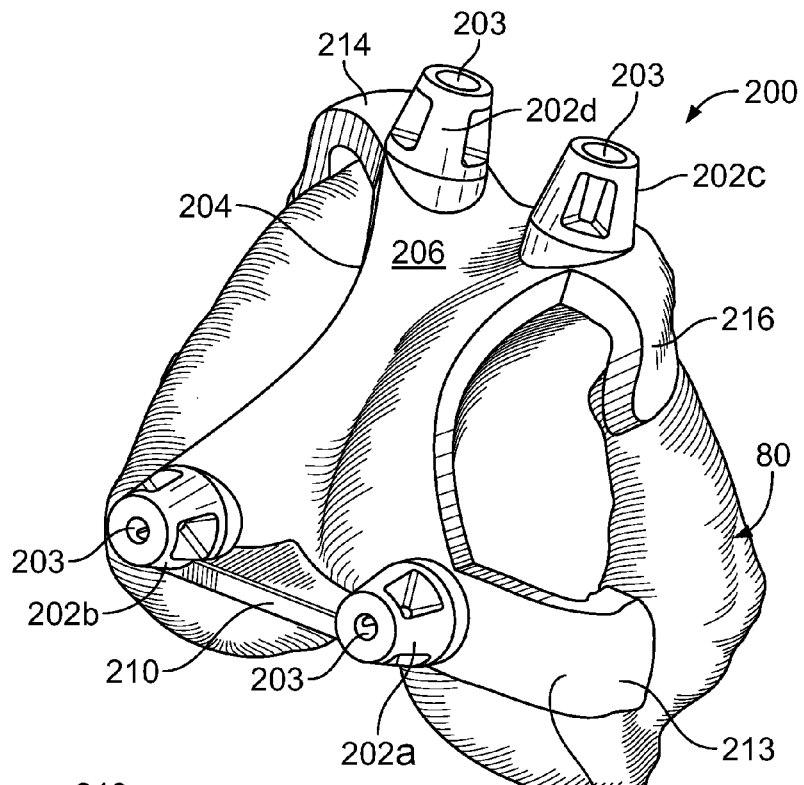
FIGS. 5-7 are environmental perspective views of a patient-specific direct anterior femoral CT guide according to the present teachings.
Figure 6:
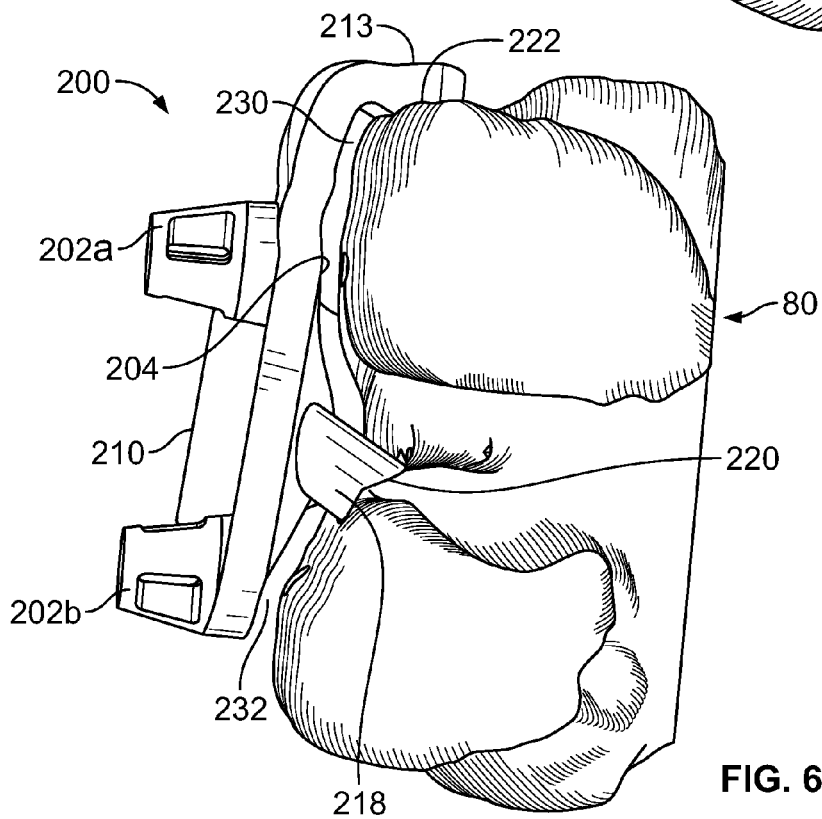
Figure 7:
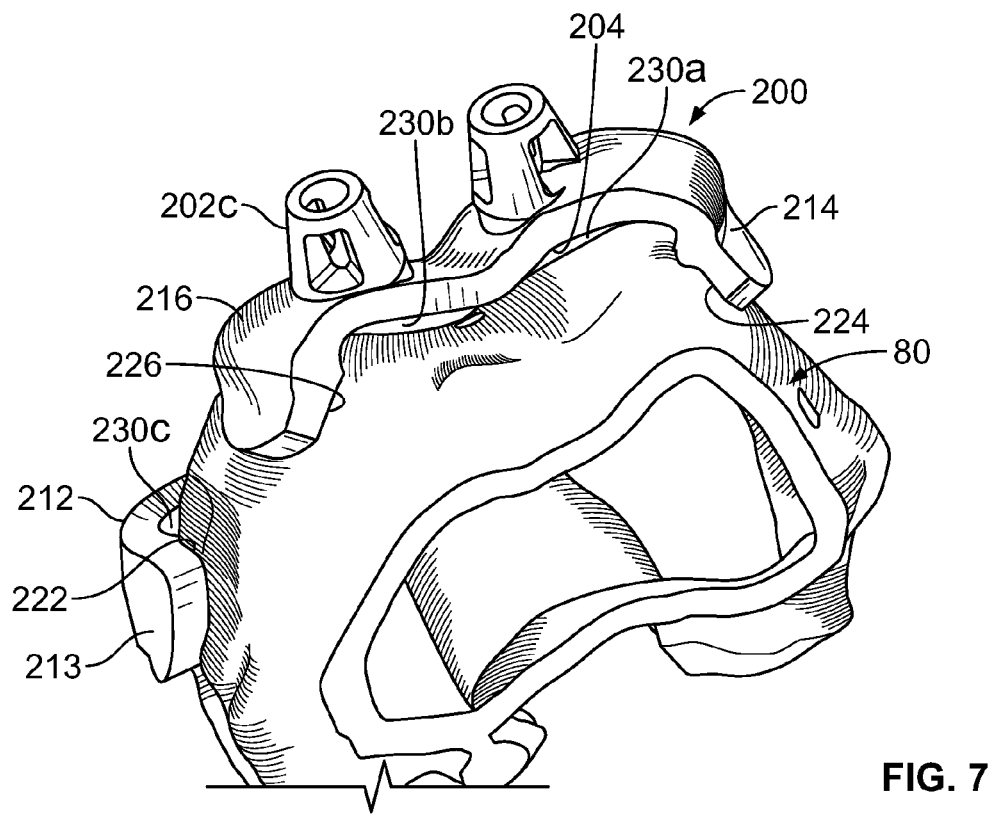
Figure 7A:
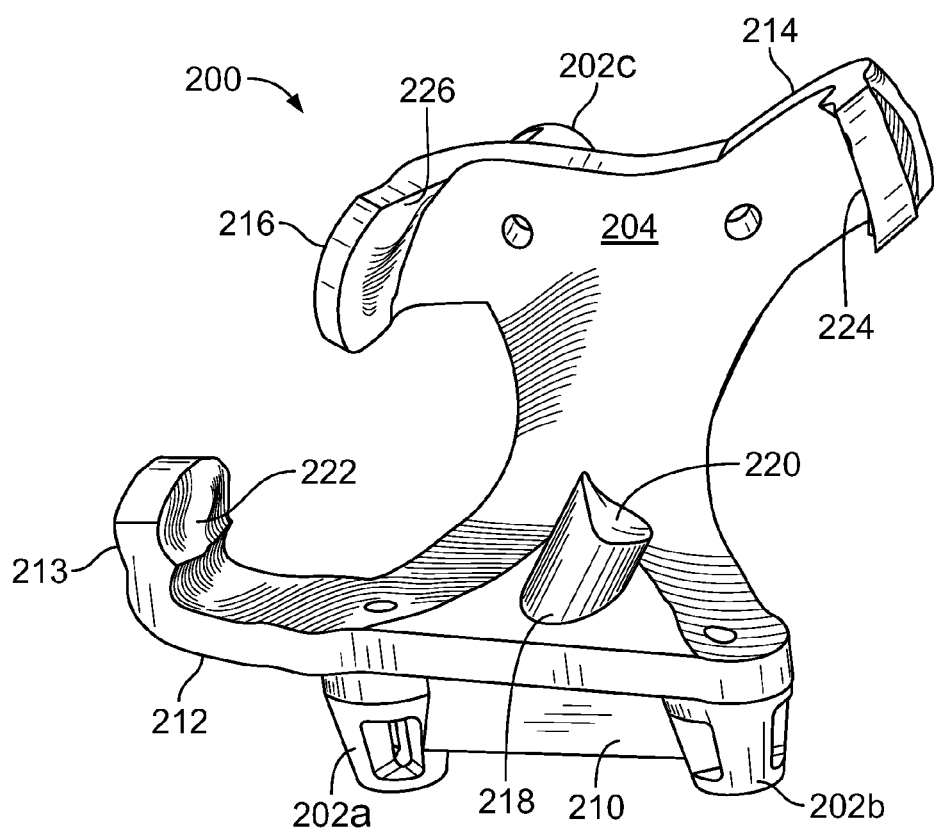
FIG. 7A is a bottom perspective view of the patient-specific direct anterior femoral CT guide of FIG. 5.

As generally discussed above, the inner surface 104 is patient-specific and configured to mirror the underlying bone 84 with an offset from the bone 84 to provide clearance for articular cartilage 82 or other soft tissue in areas where such soft tissue is found or retained over the bone. The offset is illustrated in FIGS. 3 and 4, wherein a gap 130 is shown to provide clearance for the articular cartilage 82 of the medial condyle and a gap 132 is shown to provide clearance for the articular cartilage 82 of the lateral condyle. Actual and direct bone contact is made at various discrete (non-contiguous) surface areas of the femoral CT guide that are shown in FIGS. 2 and 2A at 120, 122, 124 and 126 for direct bone registration. More specifically, the femoral CT guide 100 includes an extension 118 extending at an angle away from the inner surface 104 of the femoral CT guide 100 and configured to be directed toward the intercondylar notch 86 of the femur 80 and offset toward the lateral edge of the intercondylar notch 86 to provide clearance for and avoid the posterior cruciate ligament (PCL) of the femur 80, as shown in FIG. 3. In this regard, the orientation, size and length of the extension 118 are patient-specific and designed during the preoperative plan of the patient based on the medical scans of the patient. The extension 118 includes a first surface contact area 120 (intercondylar notch surface contact area), which is designed to be patient-specific and contact and mate with a corresponding bone portion 87 (no cartilage) of the intercondylar notch 86 for direct bone registration.

With continuous reference to FIGS. 1C-4, a second (or distal medial) patient-specific surface contact area 122 is provided at the inner surface of the pad portion 113 for nestingly mating with a corresponding portion of the medial surface of the bone 84 for direct bone registration. Additional third and fourth (or lateral and medial anterior) patient-specific surface contact areas 124, 126 are provided under corresponding lateral and medial anterior portions 114, 116 of the femoral CT guide, as shown in FIGS. 1C, 2, 2A, 3 and 4 for direct bone registration. The lateral anterior portion 114 can be elongated along an axis A, which is oriented at an angle β relative to an axis B that passes through the centers of the anterior guiding formations 102c, 102d, as shown in FIG. 4. The angle β and the length of lateral anterior portion can be selected during the preoperative plan such that the contact area 124 under the lateral anterior portion 114 can reach and contact directly a mating bone area that is not covered by natural cartilage or other soft tissue, as discussed above. In some embodiments, the angle β, as shown in FIG. 4, can be selected to be about 135 (180-45) degrees.

With continuous reference to FIGS. 1C-4, the fourth contact area 126 is also patient-specific and designed and configured to mate with a corresponding bone surface that is not covered by natural cartilage or other soft tissue for direct bone registration. The patient-specific surface contact areas 120, 122, 124 and 126 discussed above are exemplary. It is contemplated that either fewer or additional surface contact areas can be provided and in different locations, using different arms, extensions or medial and lateral portions for support.

Referring to FIGS. 5-7A, a patient-specific direct anterior femoral CT guide is illustrated. The femoral CT guide 200 is similar to the femoral CT guide 100, but is configured to be mounted directly anteriorly and not anteriorly-medially. Elements that are similar between the two guides 100 and 200 are referenced with numerals 1XY and 2XY respectively, and their description is not repeated. In summary, the direct anterior femoral CT guide 200 can include a reinforcing element 210, an arm 212 and a plurality of patient-specific discrete or non-contiguous surface contact or registration areas for mating with corresponding bone areas that are naturally devoid of articular cartilage, such as, for example, the contact areas 220, 222, 224, and 226 illustrated in FIG. 7A. Further, the patient-specific inner surface 204 is offset from the bone of the femur 80 for providing clearance for articular cartilage or other soft tissue. Such clearance is indicated by gaps 230, 232 in FIG. 6, and gaps 230a, 230b, and 230c in FIG. 7.

Figure 8:
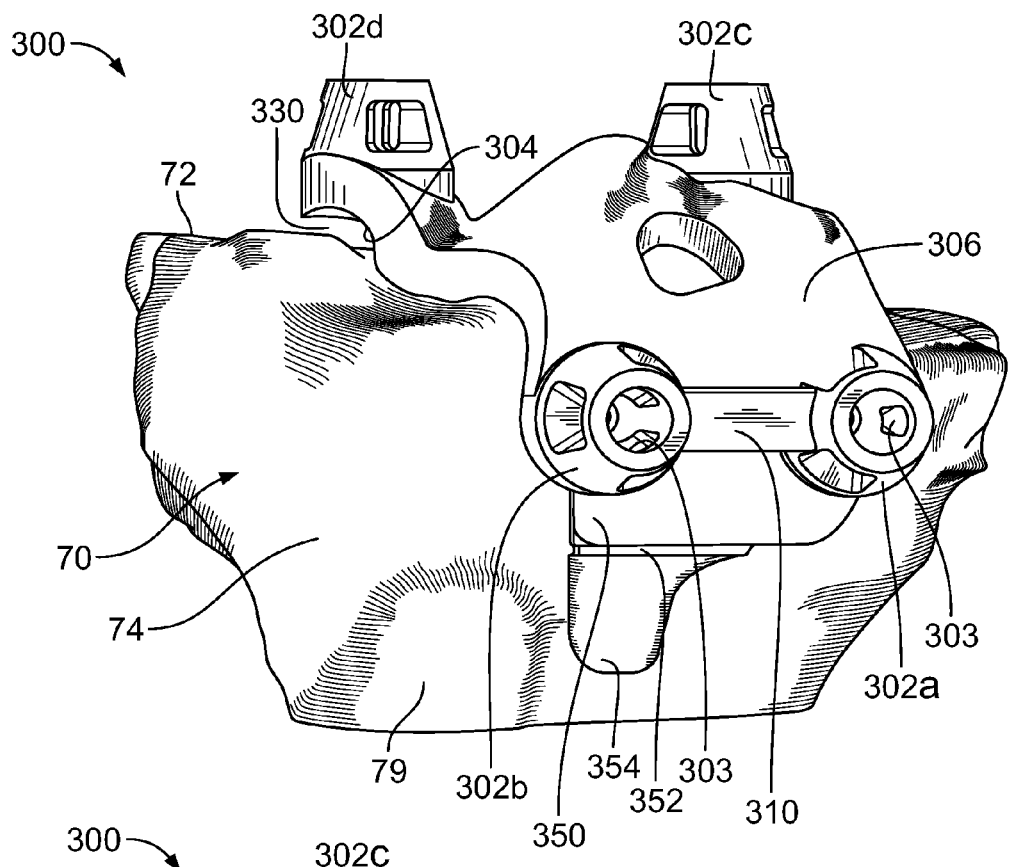
FIG. 8 is an environmental perspective view of a patient-specific anterior-medial tibial CT guide according to the present teachings.
Figure 9:
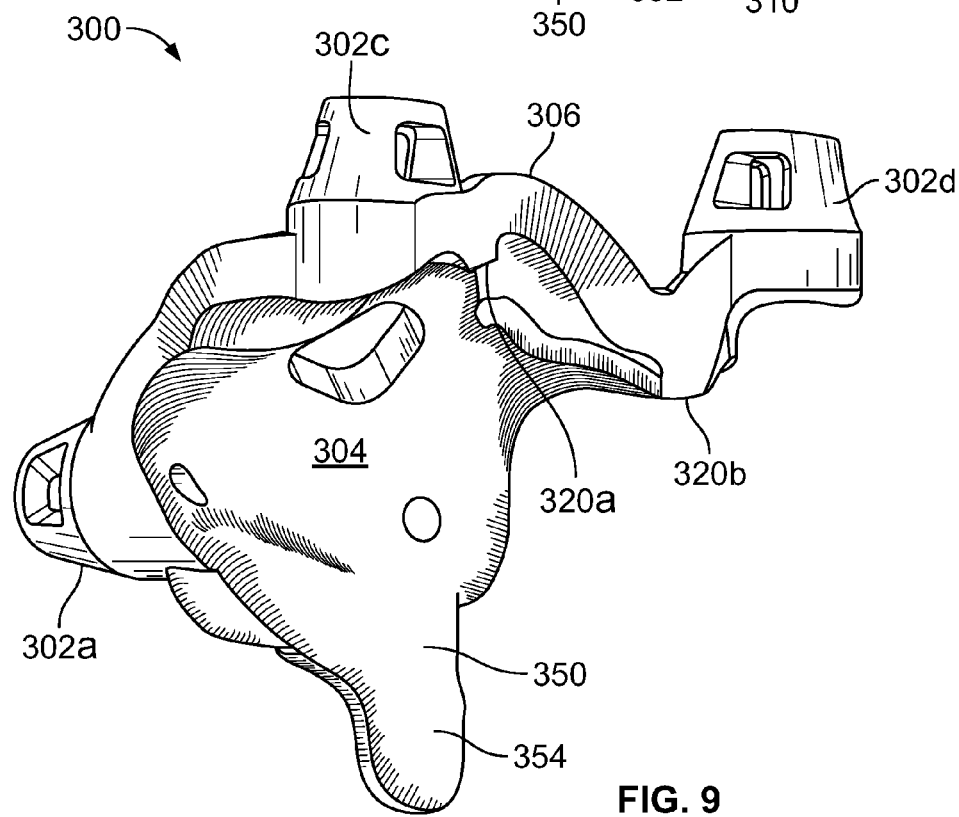
FIG. 9 is a perspective view of the patient-specific anterior-medial tibial CT guide of FIG. 8.
Figure 10:
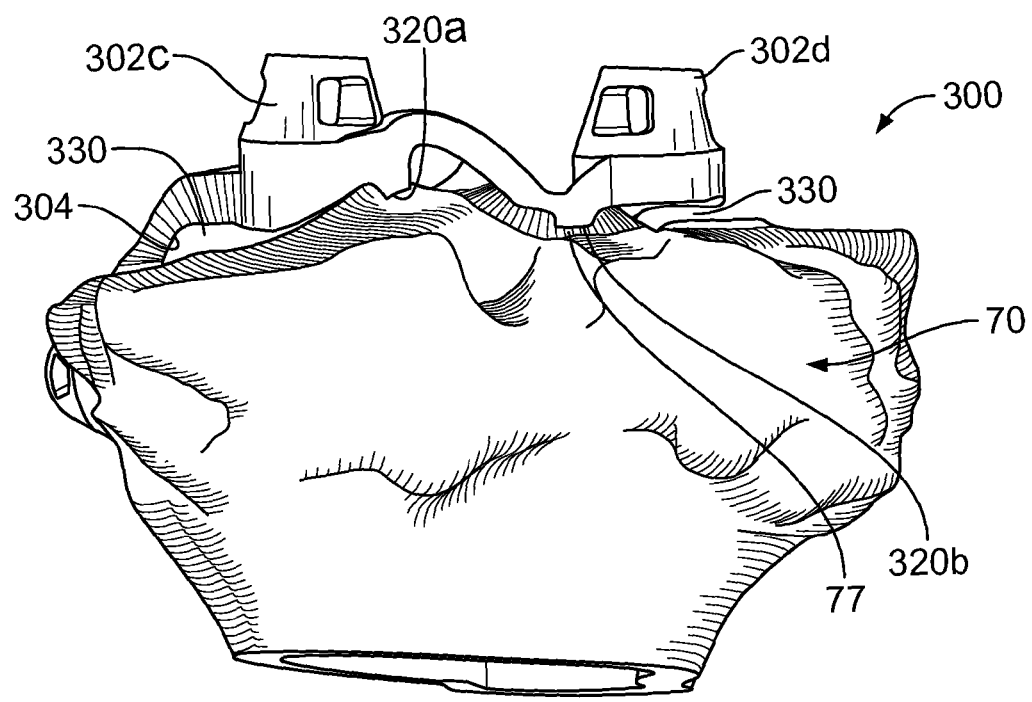
FIG. 10 is another environmental perspective view of the patient-specific anterior-medial tibial CT guide of FIG. 8.
Figure 11:
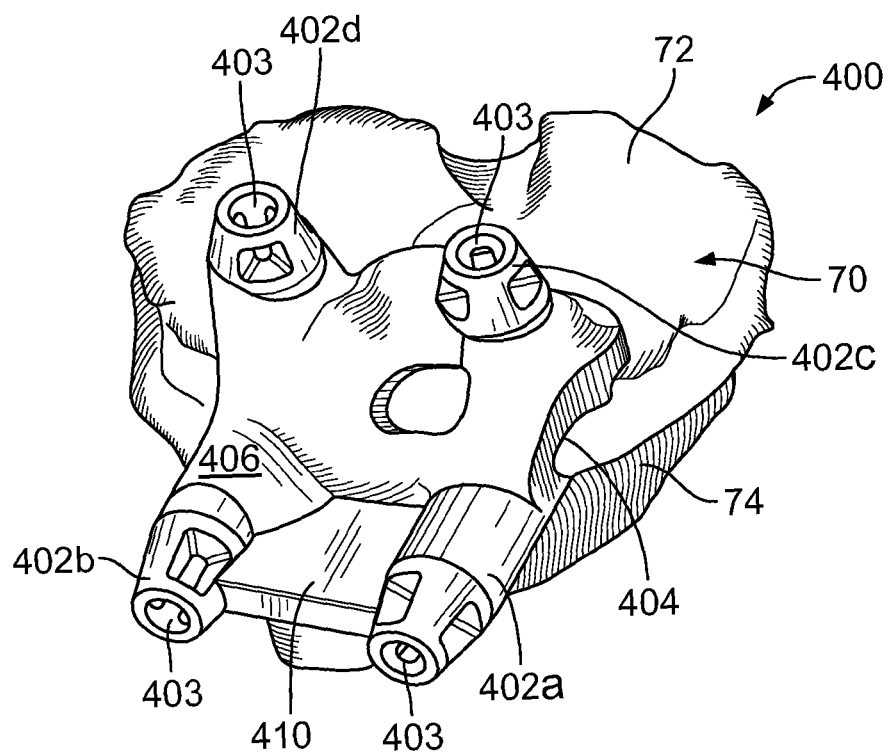
FIG. 11 is an environmental perspective view of a patient-specific direct anterior tibial CT guide according to the present teachings.
Figure 12:
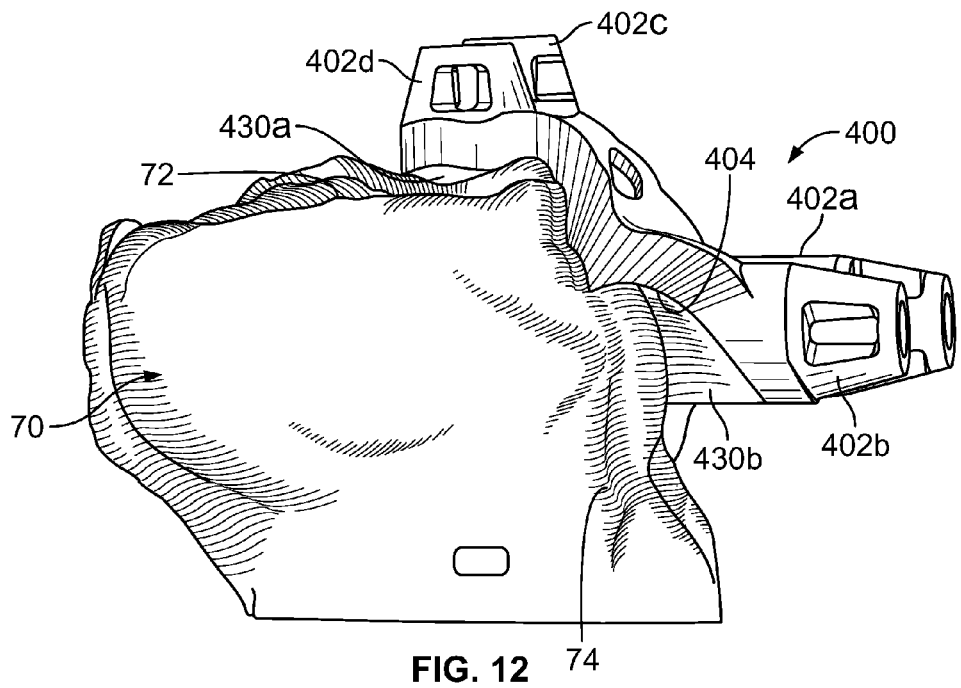
FIGS. 12 and 13 are additional environmental perspective views of the patient-specific direct anterior tibial CT guide of FIG. 11.
Figure 13:
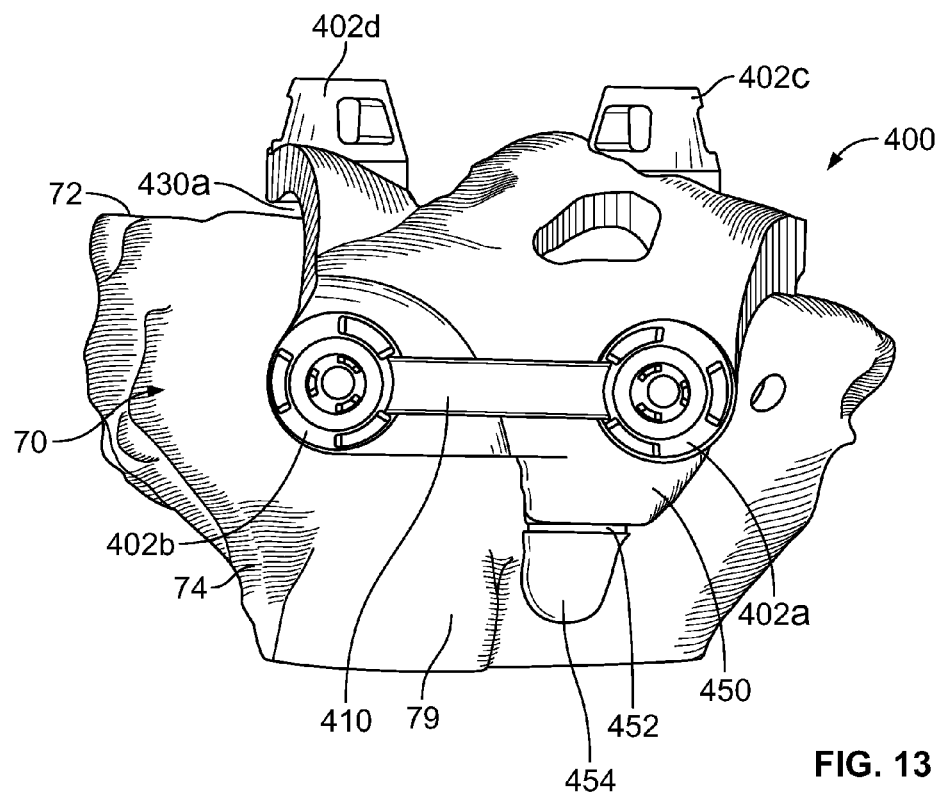

Referring to FIGS. 8-13, patient-specific tibial CT guides 300 and 400 will be described. The tibial guide 300 is shown in FIGS. 8-10 and is configured for anterior-medial placement on the patient's tibia 70. The tibial guide 400 is shown in FIGS. 11-13 and is configured for direct anterior placement on the patient's tibia 70. It is noted that a patient-specific physical model of the patient's tibia is shown in FIGS. 9-13. Each of the tibial CT guides 300, 400 includes a corresponding pair of anterior guiding formations (302a, 302b) and (402a, 402b) and a corresponding pair of proximal guiding formations (302c, 302d) and (402c, 402d). Each guiding formation has a guiding bore 303 or 403 corresponding to the tibial CT guide 300 or 400.

As discussed above generally in connection with the CT guides, the tibial CT guides 300, 400 include a reinforcing element 310, 410 extending between the pair of corresponding anterior guiding formations (302a, 302b) and (402a, 402b). Each tibial CT guide 300, 400 includes an anterior flange 350, 450 extending distally away from the anterior guiding formations (302a, 302b), as discussed below.

The patient-specific inner surface 304, 404 of the corresponding tibial CT guide 300, 400 is designed and configured to mimic and mirror the surface of the bone of the tibia but offset from the bone to provide clearance for articular cartilage or other soft tissue. Articular cartilage is found on the proximal surface 72 of the tibia, while the anterior surface 74 of the tibia 70 is a bone surface for direct contact with the CT guide, except as discussed below for avoiding various ligaments and in particular the patella tendon. Additionally, very little, if any, cartilage is found over the spine area 77 of the tibia, and the anterior cruciate ligament (ACL) is typically removed. Accordingly, the spine area 77 can also serve for direct bone registration, as shown in FIG. 10, where first and second surface contact areas 320a, 320b for direct bone registration are shown. Similar direct bone registration areas for the tibial CT guide 400 are hidden from view in FIGS. 11-13.

With continued reference to FIGS. 8-13, each of the tibial CT guides 300, 400 can include a corresponding anterior flange 350, 450 extending distally over the anterior surface 74 of the tibia 70 and registering directly on the bone. The anterior flange 350, 450 can be shaped to follow the tibial tubercle 79 without interfering with or going over it. In this regard, the anterior flange 350, 450 provides additional direct bone registration for mounting the tibial CT guide 300, 400 on the tibia 70 intraoperatively. A distal portion of the anterior flange 350, 450 can form a frangible tab 354, 454, which can be optionally broken off or cut off/clipped off by the surgeon based on intraoperative conditions and preferences. A score line or groove or other weakened line 352, 452 can be provided for ease of removal of the tab 354, 454. In some embodiments, the anterior flange 350, 450 can extend distally from the anterior guiding formations (302a, 302b), (402a, 402b) by about 1.5 cm, for example, and the tab 354, 454 can be about 0.5 cm in length. In some embodiments, the tab 354, 454 can be modularly coupled to the anterior flange 350, 450. Additional details for alignment/resection guides with frangible and/or modularly coupled portions are disclosed in commonly assigned and co-pending U.S. patent application Ser. No. 12/571,969, filed Oct. 1, 2009 and published as 2010-0087829 on Apr. 8, 2010, the disclosures of which are incorporated herein by reference.

Referring to FIGS. 8-10, soft tissue clearance areas for the articular cartilage of the proximal surface 72 of the tibia are illustrated as gaps 330 between the tibial CT guide 300 and the tibia 70. Similar clearance areas between the inner surface 404 for the tibial CT guide 400 and the proximal surface 72 of the tibia 70 are illustrated at 430a in FIG. 12. An additional clearance area 430b is formed by designing a cutout or bigger offset in the inner surface 404 of the tibial CT guide 400 under the anterior guiding formation 402b to provide clearance for the patella tendon. A similar cut out for patella tendon clearance is formed under the anterior guiding formation 302b of the tibial CT guide 300, but is not visible in the views shown in FIGS. 8-10.

Generally, the patient-specific alignment guides (CT guides) described herein can be manufactured by obtaining images of the bone surface of the patient using a CT or other imaging method and forming an inner surface of the patient-specific alignment guide to conform and mimic the bone surface. Further, the inner surface is constructed to be offset from the bone surface to provide clearance and avoid articular cartilage, ligaments and other soft tissue when it is mounted on the patient's bone. A plurality of patient-specific contact areas for direct bone registration are constructed on various portions of the alignment guides. In some cases, extensions or arms are constructed to provide support for corresponding surface contact areas for direct bone registration.

Example embodiments are provided so that this disclosure is thorough, and fully conveys the scope to those who are skilled in the art. Numerous specific details are set forth such as examples of specific components, devices, and methods, to provide a thorough understanding of embodiments of the present disclosure.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A patient-specific alignment guide for joint arthroplasty comprising:
   a patient-specific inner surface configured to be offset from and mimic a bone surface so that a majority of the patient-specific inner surface does not make contact with the bone surface, the patient-specific inner surface forming a clearance under the patient-specific inner surface for soft tissue overlying the bone surface; and
   a plurality of patient-specific contact areas formed on the patient-specific inner surface and configured to contact the bone surface without intervening soft tissue; and
   an extension extending from the patient-specific inner surface, the extension comprising a patient-specific contact surface configured to contact the bone surface without intervening soft tissue.

2. The patient-specific alignment guide of claim 1, further comprising: a plurality of patient-specific guiding formations having corresponding bores for guiding alignment pins or other tools therethrough.

3. The patient-specific alignment guide of claim 2, further comprising: a reinforcing element between a first patient-specific guiding formation and a second patient-specific guide formation of the plurality of patient-specific guiding formations.

4. The patient-specific alignment guide of claim 2, wherein the patient-specific alignment guide further comprises: an anterior flange extending distally from a first patient-specific guiding formation and a second patient-specific guiding formation of the plurality of guiding formations, and wherein the anterior flange comprises a patient-specific surface contact area for direct bone registration.

5. The patient-specific alignment guide of claim 4, wherein the anterior flange includes a removable portion.

6. The patient-specific alignment guide of claim 5, wherein the removable portion is frangible along a score line.

7. The patient-specific alignment guide of claim 4, wherein the plurality of patient-specific contact areas include at least one contact area configured to contact a tibial spine.

8. The patient-specific alignment guide of claim 4, wherein the patient-specific alignment guide includes a cutout under one of the plurality of patient-specific guiding formations configured to provide clearance for a patella tendon.

9. A patient-specific alignment guide for joint arthroplasty comprising:
   a patient-specific inner surface configured to be offset from a bone surface so that a majority of the patient-specific inner surface does not make contact with the bone surface, the patient-specific inner surface forming a clearance under the patient-specific inner surface for soft tissue overlying the bone surface;
   a plurality of patient-specific contact areas formed on the patient-specific inner surface and configured to contact the bone surface without intervening soft tissue;
   an extension extending from the patient-specific inner surface, the extension comprising a patient-specific contact surface configured to contact the bone surface without intervening soft tissue;
   a first pair of patient-specific guiding formations having corresponding bores for guiding a tool therethrough; and
   a second pair of patient-specific guiding formations having corresponding bores for guiding the tool therethrough.

10. The patient-specific alignment guide of claim 9, wherein the first pair of guiding formations are proximal guiding formations and the second pair of guiding formations are anterior guiding formations.

11. The patient-specific alignment guide of claim 10, wherein the plurality of patient-specific contact areas includes:
   a first surface contact area configured to contact a tibial spine portion on a proximal surface of a tibia; and
   a second surface contact area configured to contact an anterior bone surface of the tibia.

12. The patient-specific alignment guide of claim 10, wherein the patient-specific alignment guide includes a cut-out under at least one of the guiding formations, and wherein at least one of the guiding formations is configured to provide clearance for a patella tendon.

* * * * *